United States Patent [19]

Bacon et al.

[11] Patent Number: 5,030,420
[45] Date of Patent: Jul. 9, 1991

[54] APPARATUS FOR OXYGEN DETERMINATION

[75] Inventors: John R. Bacon, Sylvan, N.C.; James N. Demas, Charlottesville, Va.

[73] Assignee: University of Virginia Alumni Patents Foundation, Charlottesville, Va.

[21] Appl. No.: 825,735

[22] Filed: Feb. 3, 1986

Related U.S. Application Data

[63] Continuation-in-part of Ser. No. 452,659, Dec. 23, 1982, abandoned.

[51] Int. Cl.$^5$ ................. G01N 21/64; G01N 21/77
[52] U.S. Cl. ................. 422/82.07; 128/633; 128/634; 250/458.1; 250/459.1; 422/55; 422/56; 422/91; 436/136; 436/138; 436/172; 436/175; 436/178
[58] Field of Search ............. 436/136, 138, 172, 175, 436/178, 169; 250/458.1, 459.1; 356/39, 40, 41; 128/633, 634, 664, 665, 666; 422/55, 52, 56, 83, 88, 91, 82.07, 82.08

[56] References Cited

U.S. PATENT DOCUMENTS

| Re. 31,832 | 2/1985 | Samulski | 250/459.1 X |
|---|---|---|---|
| 3,612,866 | 10/1971 | Stevens | 422/71 X |
| 3,725,658 | 4/1973 | Stanley et al. | 436/136 X |
| 4,003,707 | 1/1977 | Lubbers et al. | 436/172 |
| 4,245,507 | 1/1981 | Samulski | 374/159 |
| 4,476,870 | 10/1984 | Peterson et al. | 128/634 |
| 4,657,736 | 4/1987 | Marsoner et al. | 436/136 X |

FOREIGN PATENT DOCUMENTS 0893853 12/1981 U.S.S.R. ................. 436/136

OTHER PUBLICATIONS

Peterson et al., Rev. Sci. Instrum., vol. 51, No. 5, pp. 670-671, May 1980.
Taylor, Chemical Abstracts, vol. 90, Abstract No. 90:35990h, 1978.
Demas et al., J. American Chem. Soc., vol. 95, No. 20, pp. 6864-6865, 1973.
Teale, "Time Resolved Fluorescence Spectroscopy in Biochemistry and Biology", Ed. by Cundall et al., Plenum Press, 1983, pp. 59-80.

Primary Examiner—Robert J. Hill, Jr.
Attorney, Agent, or Firm—James Creighton Wray

[57] ABSTRACT

Quenching luminescence of the tris(4,7-diphenyl-1,10-phenanthroline)ruthenium(II) perchlorate, immobilized in a silicone rubber by oxygen is shown to be an accurate and precise method for measuring oxygen concentration in solutions and in the gas phase. Quenching can be quantitated by either lifetime or intensity quenching measurements. Strong aqueous acids and bases, complexing agents, oxidants, and reductants do not penetrate the hydrophobic polymer and, therefore, do not affect the response. Gaseous interferents, such as $H_2S$, anesthesia gases (e.g. $N_2O$, Halothane), and fluorocarbons do not affect the response. Chlorine and especially $SO_2$ cause strong, but reversible interference presumably because of electron transfer quenching. A system with a response time of less $<0.2$ s is disclosed, which is adequate for the monitoring of breathing subjects.

1 Claim, 4 Drawing Sheets ated by the Chemistry Department of the University of Virginia and NSF grant 82-06279.

This is a continuation-in-part of U.S. application Ser. No. 452,659, filed Dec. 23, 1982, now abandoned.

APPARATUS FOR OXYGEN DETERMINATION

This patent is the result of research partially supported by the Chemistry Department of the University of Virginia and NSF grant 82-06279.

This is a continuation-in-part of U.S. application Ser. No. 452,659, filed Dec. 23, 1982, now abandoned.

BACKGROUND OF THE INVENTION

This invention relates generally to oxygen determinations and more particularly has reference to methods and apparatuses for determining the concentration of oxygen in a gaseous or liquid environment based on luminscence quenching.

The determination of oxygen concentrations in gaseous samples, aqueous samples, and biological fluids has important ramifactions in medicinal, environmental and analytical chemistry. Today most oxygen measurements are based on modifications to the Clark electrode, Clark, Jr., L. C.; Trans. Am. Artif. Intern. Organs 1956, 2, 41, although the Winkler titration is also widely used, Skoog, D. A.; West, D. M.; Fundamentals of Analytical Chemistry, 3rd Edition, Holt, Rinehart and Winston, New York 1976, p. 369. The Clark electrode is easily calibrated, relatively rapid in response, and requires relatively inexpensive instrumentation. However, Clark electrodes consume oxygen and are easily poisoned by $H_2S$, proteins, and various organic compounds. In operating room use, they register large oxygen concentrations in the presence of certain anesthetics, which is a potentially fatal shortcoming, Albery, W. J.; Hahn, C. E. W.; Brooks, W. N.; Br. J. Anaesth. 1981, 53, 447.

The Winkler titration is slow and cumbersome. Further, since it is based on oxidation-reduction chemistry, interferences are numerous.

It is known that many platinum group metal complexes luminesce intensely in the red region (600–650 nm) when excited with visible light or UV light (<550 nm). Both the intensity and the lifetime of the luminescence is decreased when the complex is exposed to deactivators (quenchers). Oxygen, iron(III), copper(II), and mercury(II) are among the common quenchers. When a single quencher is present in an environment, the degree of intensity or lifetime quenching is directly related to the quencher concentration and can be used as an analytical method for determining that concentration. However, the inability of the method to discriminate among different quenchers in an environment has herefore prevented the method from being universally applicable.

The discrimination problem is particularly acute when dealing with a liquid environment. If the luminescent complexes are dissolved directly in the solution, a variety of dissolved organic and inorganic contaminants and interferents contribute to the quenching and produce erroneous indications of oxygen concentrations.

Because the luminescence quenching method presents the possibility of making oxygen determinations without the limitations inherent in the Winkler titration method and the oxygen electrode method, it is desirable to improve upon known methods and apparatuses in the luminescence quenching art in order to make the method universally applicable.

The art is largely unpredictable because there are large environmental effects on luminescence behavior. The existence of emission and quenching in one matrix in no way guarantees the material will emit in another matrix. There are generally large changes in luminescent and quenching properties ongoing from solution to solid matrices, especially at the high concentrations needed by many sensors. It would be impossible to predict the suitability of materials in solid sensor matrices even for experts having more than 20 years of experience in this art.

Luminescence phase shifts are well known by practioners in the art. Phase shift measurements were suggested at least as early as 1904, and the first successful phase shift lifetime measurement was made by E. Gaviola in 1926 (Ann. Phys. (Leipzig) 81, 23 (1926)). For a full summary of phase shift lifetime measurement see the review by F. W. J. Teale in "Time Resolved Fluorescence Spectroscopy in Biochemistry and Biology" (Ed by R. B. Cundall and R. E. Dale, Plenum Press, 1983, p. 59).

The relating of quenching and quencher concentration dates back to the work of Stern and Volmer (1931). A recent biochemical example is taken from the work of J. R. Lakowicz and G. Weber (Biochemistry 12 4161 (1973)) who used the phase shift method to quantitate the degree of deactivation of a luminescent species by oxygen. This work was not used to measure oxygen concentrations and furthermore, the system as described would not be suitable for any such measurements.

Luminescence measurement analysis for monitoring concentrations of analytes is well known in the art. One merely makes a calibration curve of intensity verses concentration. When luminescent materials are excited by a modulated excitation source, the phase shift between the excitation beam and the emission beam can be used to determine the luminescent lifetime.

Pertinent United States and foreign patents are found in Class 23, subclasses 26, 52, 83, 230, 259, 906 and 927; Class 73, subclass 19; Class 204, subclasses 1, 1Y, 192P and 195; Class 250, subclasses 71 and 361C; Class 252, subclasses 18.3CL and 301.2; and Class 422, subclasses 52, 55–58, 83, 85–88 and 92 of the Official Classifications of Patents in the U.S. Patent and Trademark Office.

Examples of pertinent patents are U.S. Pat. Nos. 998,091; 1,456,964; 2,351,644; 2,929,687; 3,112,999; 3,697,226; 3,725,658; 3,764,269; 3,768,976; 3,881,869; 3,897,214; 3,976,451; 4,054,490; 4,073,623; 4,089,797; 4,181,501; 4,231,754; 4,260,392; 4,272,249; 4,272,484; and 4,272,485.

U.S. Pat. No. 3,725,658 shows a method and apparatus for detecting oxygen in a gas stream. The apparatus employs a sensor film comprising a fluorescent material dissolved in a carrier or solvent and supported on a substrate. Oxygen contained in the gas stream is dissolved into the film and quenches the fluorescent emission, the extent of quenching being proportional to the oxygen content of the gas stream. This patent claims four organic sensor materials, i.e., pyrene, coronene, p-terphenyl, and ovalene in addition to all fluorescent materials which absorb in the 2000–6500 Å range and emit in the 3000–8000 Å range. However, phosphorescent detectors are specifically excluded as potential sensor materials because of stability problems of the then known complexes. The stability problems were primarily centered on irreversibility of phosphorescing complexes. Moreover, emission intensity and not lifetime of quenching is the method of quantitation.

Stanley and Kropp, U.S. Pat. No. 3,725,658, explicitly use liquid or grease solvents as carriers. These include mineral oil, decalin, glycerol, and Apiezon N vaccum grease (column 3, lines 50-58). In the claims section they claim only a solvent "... selected from the class consisting of mineral oil, decalin, glycerol, tetrahydrofuran, benzene, and hexane." (column 8, lines 54-56). They also mention (column 4, lines 49-56) the protection of their sensor with plastic films when the sensor is absorbed onto silica gel, alumina, etc. This is quite different from incorporating the sensor directly into a polymer.

U.S. Pat. No. 3,764,269 shows the use of a gas permeable membrane which permits diffusion of a particular gas while providing protection against adverse effects of the environment. An electrochemical device detects the concentration of gas which passes through the porous layer and activates the electrode.

U.S. Pat. No. 3,881,869 discloses the chemiluminescent detection of ozone concentration in a gas sample. The gas sample contacts an organic polymer having a backbone chain consisting of carbon atoms to produce a chemiluminescent reaction. The concentration of ozone is proportional to the intensity of light emitted by the reaction.

U.S. Pat. No. 4,089,797 discloses chemiluminescent warning capsules having an air-reactive chemiluminescent formulation encapsulated with a catalyst. Crushing the capsule mixes the air-reactive formulation and the catalyst in the external environment to produce chemiluminescence if air is present.

U.S. Pat. No. 4,272,484 uses fluorescence methods to measure oxygen content after first separating blood protein fractions and other components by use of a gas permeable membrane. U.S. Pat. No. 4,272,485 is a related disclosure which includes a carrier which transports particles through the membrane.

U.S. Pat. No. 3,112,999 discloses a method where a gas, particularly carbon monoxide, permeates a porous layer to make an indication.

U.S. Pat. No. 2,929,687 discloses a dissolved oxygen test.

U.S. Pat. No. 3,768,976 shows a polymeric film through which oxygen migrates to cause an indication.

U.S. Pat. No. 3,976,451 describes selectively permeable membranes for passing oxygen.

U.S. Pat. No. 4,260,392 shows a selectively permeable plastic tape.

U.S. Pat. No. 3,897,214 discloses reagents impregnated in plastic fibers.

U.S. Pat. No. 3,697,266 discloses a system using a graded scale for visual comparison. The comparison scale is not placed in a solution. It is merely a screen.

U.S. Pat. No. 998,091 discloses a color comparing scheme in which thickness is varied in a graded standard.

U.S. Pat. Nos. 4,181,501 and 4,054,490 disclose wedge shaped concentration sensors.

U.S. Pat. No. 2,351,644 discloses a stepped sensor.

U.S. Pat. No. 4,073,623 discloses a non-immersed sensor and standard used for visual comparisons.

U.S. Pat. No. 1,456,964 discloses light intensity comparison.

U.S. Pat. No. 4,003,707, Lubbers et al, discloses a method and apparatus for detecting oxygen wherein the detecting material is incorporated in a matrix which is permeable to oxygen but impermeable to interfering materials. Lubbers et al further discloses that the detecting material or indicator can be embedded in a foil which serves as a gas permeable membrane and a light transmissive surface by polymerization of a solution of silicone or any synthetic plastic material, such as polyvinylchloride mixed with the indicating substance. Lubbers et al also discloses that the device may comprise a plurality of small carrier particiles having the indicating substance embedded therein. Lubbers et al has a membrane which separates the reactive material in a cell from the substance being tested. Lubbers et al teaches a harsh method not amenable to more modern sensitive indicators. Reversible phosphorescing complexes are sensitive indicators, especially heavy metal atom, stabilized phosphorescing complexes wherein emissions specifically involve the metal ion. Polymerizing these complexes into selectively permeable matrices is out of the question. Methods are needed to immobilize and embed these modern complexes without physically or chemically altering their structures.

U.S. Pat. No. 3,904,373, Harper, discloses the concept of binding indicators to insoluble carriers with covalent bonding. The indicators specifically mentioned are organic chemicals. The insoluble carriers are glass mixtures. The reaction to bind the indicators needs a silicone coupling agent, refluxing and distillation apparatuses. Sensitivities of more modern indicators, such as heavy metal, atom stabilized phosphorescing complexes preclude the use of such teachings. Moreover, glass is not an optimal matrix in light of more modern insoluble carriers. What is needed is a simple diffusion method of immobilizing an indicator substance in an insoluble matrix such as silicone rubber. Such a matrix would be more versatile and amenable to a plethora of probe embodiments.

U.S. Pat. No. 4,255,053, Lubbers et al, discloses a method and apparatus for an optical measurement of the concentration of substances wherein the device includes a reference device with various concentrations of a reference material. Improvements are needed in this method because the sensor and reference are not aligned in proximate relationship. Using various calibration ranges is not a contemporaneous measurement and is cumbersome. Microscopic particles used in a matrix is suggested but single isolated particles are needed for monitoring [$O_2$] under a microscope for lifetime quenching methods. Moreover, Lubbers specifically excludes using the same material for the reference and the sensor. Column 2, lines 59-64. Furthermore, a detailed analysis of the equations shows that the design cannot be made to work with a reference that has an emission identical to reversible phosphorescing material. This is a consequence of the fact that Lubbers must separate the signals from these materials optically by wavelength while what is needed is a separation done by using either two detectors or by time multiplexing the two signals onto one detector. While Lubbers suggests using several reference indicators (column 5, 15-7), the exclusion of using the same indicator substance for reference and sensor completely overlooks the enormous advantages. These advantages include: (1) By comparing identical colors on both channels one avoids any ambiguities in the spectral sensitivity of the detector, especially if the same detector is time multiplexed between the two samples; (2) Use of the same material in both channels makes the responses largely temperature independent if they are thermally lagged to each other since the intensity of both will rise and fall together as the temperature is varied.

USSR Patent 893,853, Leningrad, discloses a method for detecting oxygen wherein the oxygen is detected by the quenching of a luminescent material. This reference describes an indicator within a silica gel. The silica gel is a highly absorbent drying agent which would draw deoxygenated water as well as residual oxygen into the silica gel. What is needed is a carrier that is gas permeable and solvent impermeable.

The remaining patents are of lesser interest.

The following publications are also of interest.

*Energy Transfer in Chemiluminescence*, Roswell, Paul and White, Journal of the American Chemical Society, 92:16, Aug. 12, 1970, pp. 4855–60; *Oxygen Quenching of Charge-Transfer Excited States of Ruthenium (II) Complexes. Evidence for Singlet Oxygen Production*, Demas, Diemente and Harris, Journal of the American Chemical Society, 95:20, Oct. 3, 1973, pp. 6864–65; *Energy Transfer from Luminescent Transition Metal Complexes to Oxygen*, Demas, Harris and McBride, Journal of the American Chemical Society, 99:11, May 25, 1977, pp. 3547–3551; Britton, *Hydrogen Ions. Their Determination and Importance in Pure and Industrial Chemistry*, D. Van Nostrand Company, Inc. (1943) pp. 338–43; and *Fiberoptics Simplify Remote Analyses*, C&EN, Sept. 27, 1982, pp. 28–30. *Porphyrins XVIII. Luminescence of (Co), (Ni), Pd, Pt Complexes*, Eastwood and Gouterman, Journal of Molecular Spectroscopy, 35:3, Sept. 1970, pp. 359–375; *Porphrins. XIX. Tripdoublet and Quartet Luminescence in Cu and VO Complexes*, Gouterman, Mothies, Smith and Caughey, Journal of Chemical Physics, 52:7, Apr. 1, 1970, pp. 3795–3802; *Electron-Transfer Quenching of the Luminescent Excited State of Octachlorodirhenate (III)*, Nocera and Gray, Journal of the American Chemical Society 103, 1971, pp. 7349–7350; *Spectroscopic Properties and Redox Chemistry of the Phosphorescent State of* $Pt_2(P_2O_5)_4H_8^{4-}$, Che, Butler and Gray, Journal of the American Chemical Society 103, 1981, pp. 7796–7797; *Electronic Spectroscopy of Diphosphine- and Diarsine-Bridget Rhodium (I) Dimers*, Fordyce and Crosby, Journal of the American Chemical Society 104, 1982, pp. 985–988.

The Demas et al articles disclose oxygen quenching of α-diimine complexes of Ru(II), Os(II), and Ir(III). 2, 2'-bipyridine, 1,10-phenanthroline and substituted derivatives are used as ligands to form the metal-ligand complexes. A kinetic mechanism for the complex oxygen interaction is proposed.

The Roswell article discusses intermolecular energy transfer in chemiluminescence.

The Britton publication discloses a wedge method for the determination of indicator constants of two-color indicators.

The C&EN article deals with PTFE control membranes in the context of laser optodes and optical fibers.

The Eastwood article describes the room temperature luminescence and oxygen quenching of Pd and Pt porphyrin complexes in fluid solutions.

The Gouterman et al article describes low temperature luminescence of Cu and VO porphyrins. Extrapolation of their data to room temperature indicates oxygen quenchable lifetimes.

The Nocera paper reports quenching of dinuclear Re species. Mononuclear and dinuclear Re complexes also have quenchable excited states.

The Che paper reports long excited state lifetimes and solution oxygen quenching of a dimeric Pt complex in solution and long-lived quenchable excited states of Rh dimers.

The Fordyce reference reports long-lived low temperature emissions of Rh(I) with bridging ligands. Rh(I) and Ir(I) data are referenced. Extrapolation of their data to room temperature suggests oxygen quenchable lifetimes.

A major problem with existing sensor materials is that they are organic molecules that generally suffer from instabilities and/or short fluorescence lifetimes, which make them relatively insensitive to oxygen quenching. While, in principle, there are long-lived phosphorescences, the extant molecules at the time of the earlier patents were all unstable and therefore unsuitable as sensors. Indeed, Stanley and Kropp (U.S. Pat. No. 3,725,648, col. 2, 1 46–50) explicitly excluded phosphorescent molecules as potential sensor materials because of the stability problems. Lubbers (U.S. Pat. No. 4,255,053 and 4,003,707) never goes on to correct (extend, change) this limitation. Therefore, new classes of more stable long-lived sensor materials are required.

A further problem with existing sensor materials is the preparation of a suitable film with the luminescent sensor. One preparation procedure evaporates the films from a solution containing polymer and luminescent sensor material; many polymers (e.g. silicones) cannot be evaporated since they are not soluble in suitable solvents. The other suggested procedure is to polymerize the luminescent sensor material with the monomer. However, most polymerizations are free radical processes that can destroy much or all of the luminescent material and create undesirable side products.

Another problem with existing technologies is that they use luminescence intensity to measure the degree of interaction with the quencher: Since the emission intensity is a function of the temperature of the film, any fluctuation in the temperature of the sensor will appear as apparent changes in the quencher concentration. A further problem is that unless a double beam arrangement is used, excitation source fluctuations appear as erroneous concentration changes.

An additional disadvantage of existing technologies is that there is no inexpensive visual method for monitoring gaseous concentrations of various species. Also, the methods of protecting sensors from the environment are limited. Furthermore, no method is suitable for measuring concentrations of dissolved gases such as oxygen in such systems as growing cells under a microscope or in the central core of a flow cytometer cell where any invasive device such as a catheter would cause the system to stop functioning.

All of the systems in the art either lack stability, suffer from a variety of interferents, lack enabling details to implement, or are merely concepts rather than working models.

SUMMARY OF THE INVENTION

The present invention overcomes the problems which exist in the prior art.

The present invention provides a method for measuring oxygen concentrations either in solutions or in the gas phase. The method is based on the shortening of the lifetime or decrease in the emission intensity, i.e., quenching, of particular metal complexes, preferably ruthenium(II) complexes with d-diimine ligands in the presence of oxygen. The oxygen concentrations can be directly related to the degree of quenching. To prevent the complexes from responding to contaminants and interferents, the complex is protected by being immobilized in a gas permeable, solvent impermeable polymer, such as a light transmissive silicone rubber.

The invention provides an oxygen concentration sensor and a graded calibration standard which can be visually compared to determine oxygen concentration. The sensor is a fluorophor immobilized in an oxygen-permeable polymer. The graded calibration standard is either tapered with thicker (brighter) portions corresponding to lower oxygen concentrations on the sensor or with higher (brighter) concentrations of a fluorophor at one end of the standard. The sensor and standard are exposed to the environment being sampled and are excited by a light source. Intensity of the light emitted by the sensor is decreased by the oxygen. The eye, or an electronic detector, is used to determine the part of the standard that has the same brightness as the sensor.

The invention also provides a method for making an oxygen sensor. The method sets out steps for immobilizing the preferred indicator, tris-(4,7-diphenyl-1,10-phenanthroline)ruthenium(II) perchlorate in a silicone rubber matrix.

An object of the invention is to provide an improved method and apparatus for oxygen determinations.

A further object of the invention is to provide a method and apparatus for oxygen determination based on luminescence quenching.

Still another object of the invention is to provide an oxygen sensor having a platinum group metal complex with $\alpha$-diimine ligands immobilized in an oxygen permeable polymer which tends to prevent interfering quenchers from interacting with the complexes.

A further object of the invention is to provide a method for measuring oxygen concentrations which is usable in both liquid and gaseous environments.

A further object of the invention is to provide an oxygen determination method which is non-destructive and relatively non-intrusive and which readily lends itself to miniaturization and automation.

Still another object of the invention is to provide a method for oxygen determination which is based on a quencher-related decrease in lifetime of the luminescence of a luminescent material and requires no reference.

Still another object of the invention is to provide a method of oxygen determination which is based on a quantitative quencher related decrease in the luminescence intensity of a luminescent material.

Yet another object of the invention is to provide an inexpensive method and apparatus for visually determining the extent of quenching.

Yet another object of the invention is to provide a method for determining oxygen concentration which involves comparing the emission intensity of a sensor to the emission intensity of a series of reference emitters.

Still another object of this invention is to solve the problems in the prior art by providing a superior system for qualitative and quantitative analysis of oxygen.

Yet still another object of this invention is to provide an oxygen sensor having an indicator immobilized in silicone rubber, wherein the indicator is a heavy metal, atom stabilized reversible phosphorescing complex and wherein the spectral emissions specifically involve the metal ion. An object of the invention is to provide an apparatus for measuring oxygen concentration comprising a sensor made of luminescent material, a polymer barrier covering the sensor, wherein the polymer is permeable to oxygen, means for exciting the sensor with a modulated light source to generate luminescence, means for measuring a phase shift of the luminescence to determine luminescence lifetime, wherein quenching related decreases in lifetime due to the presence and quantity of oxygen determine concentration of oxygen.

These and other and further objects and features of the invention are apparent in the disclosure which includes the above and below ongoing specification, claims and drawings.

DETAILED DESCRIPTION OF THE INVENTION

Figure 1:
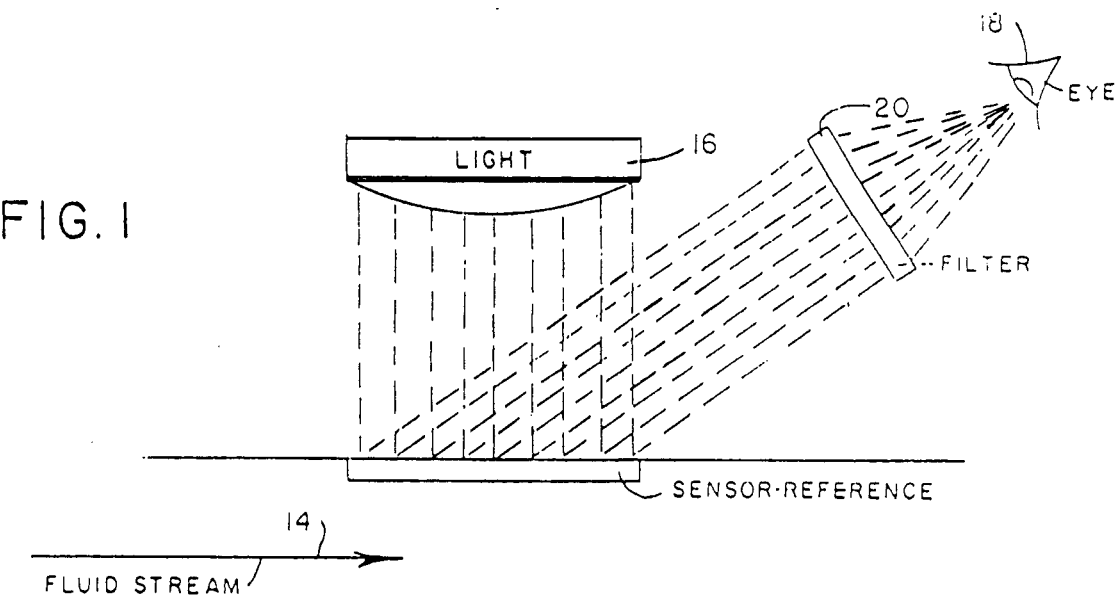
FIG. 1 is a schematic diagram, in side view, of a visual oxygen monitoring system embodying features of the present invention.
Figure 2:
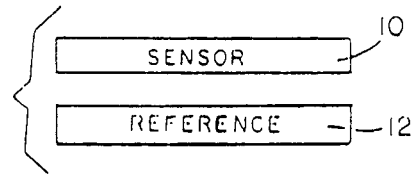
FIG. 2 is a top plan view of the sensor and reference shown in FIG. 1.

The present invention provides a method and apparatus for measuring oxygen concentrations in liquid environments and gaseous environments. The method is based on the shortening of the lifetime or decrease in the emission intensity (quenching) of certain luminescent materials in the presence of oxygen. The oxygen concentrations can be directly related to the degree of quenching in a manner well known in the art.

The luminescent materials are luminescent inorganic materials which luminesce when excited with visible or ultraviolet light and whose luminescence is quenchable by oxygen and other quenchers.

Luminescence quenching methods of analysis are based on decreases in the emission intensity or luminescence lifetimes in the presence of the quencher. If luminescence quenching is entirely diffusional, the excited state lifetimes or luminescence intensities are related to the quencher concentration by the Stern-Volmer equations.

$$\tau_o/\tau = 1 + K_{SV}[Q] \qquad (1a)$$

$$I_o/I = 1 + K_{SV}[Q] \qquad (1b)$$

$$K_{SV} = k_2 \tau_o \qquad (1c)$$

where $\tau$'s and I's are luminescence lifetimes and intensities respectively. The subscript "o" denotes the value in the absence of quencher. $k_2$ is the bimolecular quenching constant. $K_{SV}$ is the Stern-Volmer quenching constant. Plots of $\tau_0/\tau$ or $I_0/I$ versus [Q] will be linear with identical slopes of $K_{SV}$.

In principle, either Stern-Volmer equation could be used to analytically determine concentrations of a variety of quenchers. In practice, an excited state that is susceptible to quenching by one species is generally susceptible to quenching by a variety of materials, and the number of interferents is so large as to make solution luminescence quenching largely unusable. In order for luminescence quenching to be a viable analytical method, potential interferent quenchers must be excluded from the sensor while allowing rapid penetration and equilibration of the quencher to which the sensor must respond.

The preferred luminescent materials are principally platinum group metal complexes, specifically, ruthenium, osmium, iridium, rhodium, palladium, platinum, rhenium and chromium complexes with α-diimine ligands. In most instances, the tris complexes are used, but it is recognized that mixed ligand complexes can also be used to provide a degree of design flexibility not otherwise available. Suitable ligand metal complexes include complexes of ruthenium(II), osmium(II), iridium(III), rhodium(III), and chromium(III) ions with 2,2'-bipyridine, 1,10-phenanthroline, 4,7-diphenyl-(1,20-phenanthroline, 4,7-dimethyl-1,10-phenanthroline, 4,7-disulfonated-diphenyl-1,10-phenanthroline, 5-bromo-1,10-phenanthroline, 5-chloro-1,10phenanthroline, 2-2'-bi-2-thiazoline, 2,2'-bithiazole, and other α-diimine ligands. These materials are all either heavy metal atom stabilized phosphorescences, d-d emissions, or charge transfer (CT) emissions. None of these classes of materials were considered in any prior patent. The use of metal atom stabilization or new classes of emission types produce photochemically and chemically stable materials that are an entirely new concept in sensor technology.

Other suitable systems could include prophyrin or phthalocyanine complexes of $VO^{2+}$, $Cu^{2+}$, $Zn^{2+}$, $Pt^{2+}$ and $Pd^{2+}$ or dimeric Rh, Pt, or Ir complexes. Suitable ligands would be etioporphyrin, octaethylporphin, porphin and phthalocyanine.

To prevent the complexes from responding to contaminants and interferents, the complex is protected by being immobilized in a gas permeable, solvent impermeable polymer. Preferred polymers include plexiglass, polyvinylchloride (PVC), polystyrene, polycarbonate, latex, fluorinated polymers, such as Teflon, polyvinylidene fluoride, poly(tetrafluoroethylene propylene), cation and anion exchange resins, and silicone rubbers, such as GE RTV SILASTIC 118, which is very temperature resistant. A sensor using SILASTIC 118 exhibits a substantial change in lifetime or intensity of luminescence on going from an oxygen saturated environment to deoxygenated environment. The precision and accuracy of oxygen determinations is about two percent and the same responses are obtained for both lifetime and intensity quenching measurements. It responds rapidly to changes in both gas phase and solution dissolved oxygen concentrations. The plexiglass and PVC systems have lower oxygen sensitivities and are, thus, suitable for determinations at high, i.e., above atmospheric oxygen pressures. Commercially available silicone rubber has a high permeability of oxygen and excludes highly polar compounds and hydrated ions which is why its use in the present invention is desirable.

The preferred oxygen sensor uses tris (4,7-diphenyl-1,10-phenanthroline)ruthenium(II) perchlorate immobilized in the SILASTIC 118 material.

The luminescent complexes can be uniformly diffused into the polymer from dichloromethane and/or alcohol solutions. This procedure produces a more uniform and reproducible film than evaporation techniques. The method of diffusion into a preformed polymer is different from the procedures suggested for any type of film preparation described in the prior art.

The metal complexes can be mechanically or chemically incorporated into the polymer matrix. In one embodiment, the complex molecules are chemically attached to the backbone of the matrix. Either a covalent or an ionic attachment of the complex to the polymer can be used. For example, cation exchange resin bound Ru(II) complexes exhibit high sensitivity to gas phase oxygen quenching.

Chemical modification of an otherwise hydrophyllic surface by chemical silinization improves sensor operation. Chemical modification of the surface to prevent transfer of unwanted matter to the sensor as well as covalent linkage of the sensor are both valuable methods for preventing leaching of the sensor material into the solvent with loss of operational characteristics.

Using microscopic beads for monitoring concentrations under a microscope is an entirely new concept and couples well with the established techniques of microspectrofluorometry. This approach is especially viable as a lifetime rather than intensity approach since the lifetime corresponds directly to a calibration curve and no reference is necessary. The beads are not embedded in any film making them more advantageous than previously known beads. Embedding the beads in a film precludes the ability to use them to measure concentrations in vivo or in tiny flowing systems such as flow cytometry.

The completed sensor is an integral device having the luminescent material incorporated directly into the self-supporting polymer barrier system. It can be in the form of a strip, a block, a sheet, a microsphere, a film or a laminate and it can be either solid or hollow. If desired, the sensor can be a thin sensing layer diffused onto a thick plate. An overcoat of a less reactive polymer can be used to further reduce interactions within the solvent or quenchers.

To reduce expenses, it is desirable that the sensor be in the form of reusable polymer coated cuvettes which are highly durable.

In use, the sensor is exposed to the liquid or gaseous environment being sampled. Because the polymer material has a relatively high permeability to oxygen, the oxygen will permeate through the material and interact with the luminescent material to act as a quencher. However, the polymer will exclude most common ionic and organic interferents and contaminants.

In an alternative embodiment, the sensor is excited by a modulated light source and a phase shift measurement is made of the luminescence to yield the lifetimes.

The quenching-related decrease in the intensity or lifetime of luminescence is measured and that measurement is used to determine the concentration of oxygen in the environment. By measuring the luminescence lifetime or intensity using a back scattering technique, interferences caused by strong scattering or absorbing solutions are eliminated.

The present invention provides a particularly desirable means for oxygen determination because it is noninvasive and does not consume oxygen. It is linear over an extremely wide range of oxygen concentrations or partial pressures and readily lends itself to miniaturized and automated analyses.

Test results have demonstrated that the present invention is sensitive, selective and readily implemented. With the preferred combination of metal complex and polymer matrix, a material has been prepared that shows a 3000 percent increase in luminescence lifetime ongoing from an oxygen saturated aqueous environment to a nitrogen saturated environment. Response time is subsecond to minutes depending on film thickness. The same metal complex-polymer sensor responds equally well to gas phase oxygen concentrations. Films of 0.001" thickness have been shown to respond in <1/6 sec. and follow faithfully the oxygen concentrations in the respirations of humans.

The ability of the polymer to protect the complex from interferents was shown by introducing a film into a concentrated solution of iron(III). Normally iron(III) is an excellent quencher of unprotected complexes. Yet, even at the high iron(III) concentrations used, there was no detectable quenching. Strong acid, strong base, complexing agents (EDTA), and detergents (NaLS) were likewise without effect. The sensor is also immune to any deactivation by common anesthetic gases, such as Halothane and nitrous oxide at concentrations well above those used medically.

Applications for the present invention include: (1) measuring dissolved oxygen in aqueous samples and in organic solvents; (2) determining the oxygen for biochemical oxygen demand (BOD) measurements; (3) measuring levels of oxygen in blood both in vitro and in vivo using a fiber-optic probe; (4) measuring oxygen levels in air samples (e.g., mines, industrial hazard areas, oxygen tents, high pressure oxygen burn treatment and decompression chambers, industrial reactors, space capsules, etc.); (5) measuring low oxygen levels in vacuum systems (i.e., a low cost vacuum gauge); and (6) monitoring low oxygen levels in various chemical reaction vessels and other systems purged with inert gas.

An application in Category 1 would include pollution monitoring of waste water.

The application in Category 2 is especially interesting in view of the above described test using iron(III). Iron(III) is added as a nutrient in BOD determinations. However, tests have shown that iron(III) concentrations hundreds of times larger than would be encountered in BOD analyses have no detectable quenching effect. BOD determinations using quantitative intensity monitoring have been implemented.

The Category 3 applications could involve, for example, the placing of a sensor at the end of a fiber optic catheter for use in following oxygen concentrations in blood vessels and tissues as the heart is beating. Such a system has great safety as there is no electrical connection to the patient.

Advantages of the present invention are that it is a non-destructive and relatively non-intrusive method and that a common system can be used to measure oxygen in polluted, murky water, air samples, vacuum systems, and other diverse types of systems. The invention is operable at high temperatures in the range of about $-300°$ F. to about $400°$ F.

In addition, the system lends itself readily to measurements on very small sample size ($<50$ $\mu L$), instrumental miniaturization, and automation. By encapsulating the complex probe in microscopic beads, oxygen concentrations can be measured under a microscope in growing cellular samples.

Quantitative intensity and lifetime methods for measuring oxygen concentrations are accurate and precise. However, there are many times when a semiquantitative or qualitative method of even lower cost is desirable.

To avoid the cost of a more elaborate instrument the present invention further provides a low cost visual detection system with an internal reference for semiquantitative or qualitative oxygen monitoring.

In the present invention, the human eye is used as the detector. The scheme is similar in application to pH paper except that one monitors oxygen concentrations by comparing the emission intensity of the sensor in the gas or liquid environment to a series of reference emitters in that environment. Although suitable for semiquantitative of oxygen concentrations, the system is also usable as a go - no go system where instantaneous visual discrimination between pure oxygen, air, or an oxygen-free system is required.

A schematic diagram of this system is shown in FIGS. 1 through 4.

A luminescent oxygen sensor 10 and a reference emitter 12 are placed side by side in the sample fluid or gas environment 14. The sensor 10 includes a fluorophor immobilized in an oxygen-permeable support, e.g., a polymer. The sensor 20 luminesces when the fluorophor is excited by a light source 26. The intensity of the emitted light is decreased by oxygen in the environment 14 which serves as a quencher.

The human eye can easily judge the differences in intensity of the emitted light when the sensor film is exposed to pure $N_2$, air and $O_2$ environments.

The estimation of the oxygen concentration beyond air, $O_2$ or $N_2$ is improved by using a reference emitter 12 which is a concentration or optical density graded calibration standard. In the standard, the same fluorophor as used in the sensor 20 would be immobilized in a rigid polymer, e.g., plexiglass, which shows limited permeability to $O_2$. The fluorophor is distributed in the polymer in areas having different luminescence levels.

The reference emitter 12 next to the sensor 10 provides reference concentration information by emitting reference luminescence levels. The differences in luminescence between the sensor 10 and the reference 12 are visually determined by the human eye 18. An optional blocking filter 20 can be positioned between the eye 18 and the sensor 10 and reference 12 to improve viewing contrast by removing scattered excitation light. In addition, a filter (not shown) over the light source may be used to improve viewing by limiting excitation wavelengths.

Figure 3:
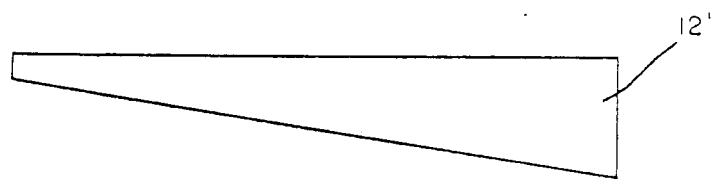
FIG. 3 is a detailed schematic diagram of a reference used with the system shown in FIGS. 1 and 2.
Figure 4:
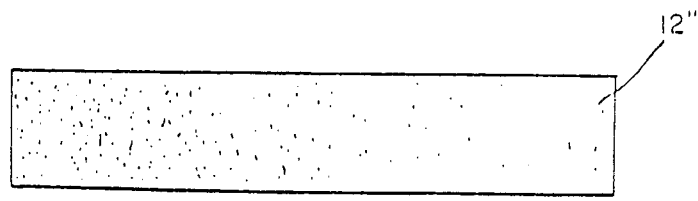
FIG. 4 is a detailed schematic diagram of an alternative reference used with the system shown in FIGS. 1 and 2.

In one embodiment, the standard 12' has a tapered wedge shape as shown in FIG. 3. The luminescence intensity at each point is determined by the thickness of the standard 12'. The thicker, i.e., brighter, portions correspond to lower oxygen concentrations on the sensor 10. A non-uniform slope on the wedge improves the linearity of calibration.

In an alternative embodiment, the standard 12" is a concentration graded reference with the concentration of fluorophor contained therein increasing from one end to the other. The higher, i.e., brighter, concentrations correspond to lower oxygen concentrations on the sensor. In the graded standard 12" shown in FIG. 4, the relative concentration of the fluorophor is indicated by the dot density. The sensor 12" is of uniform thickness.

The graded concentration standard 12" can be formed by withdrawing a polymer film from a solution containing the fluorophor material. The areas of the film which remain longer in the solution contain greater concentrations of the fluorphor.

In the preferred embodiment, the sensor 10 and the reference 12 are formed with identical luminescent materials. This ensures that the emission colors are the same and that the observer will only be comparing intensities.

Fluorophors suitable for use in the present invention include, but are not limited to, the metal complexes discussed above. The preferred material is tris(4,7-diphenyl-1,10-phenanthroline)ruthenium(II) perchlorate immobilized in a silicone rubber polymer matrix. One also may use tris(disulfonated-(4,7-diphenyl-1),10-phenanthroline) ruthenium(II), and (disulfonated-4,7-diphenyl-1,10-phenanthroline)bis(1,10-phenanthroline)-ruthenium(II). Other fluorophors and polymer matrices will give different sensitivities.

The system shown in the figures is used by allowing the oxygen in the environment 14 to impinge upon the sensor 10 and reference 12. The support matrix in the sensor 10 is permeable to oxygen, and thus allows the oxygen to quench the luminescent material. The matrix in the reference 12 restricts oxygen access to the fluorophor material therein. The luminescence of the quenched sensor 10 is then compared to the luminescence of the reference 12. The area of the reference 12 having the same luminescence as the sensor 10 is then visually selected. Knowledge of the amount of luminescent material present in the selected area is used to determine the amount of oxygen present in the environment 14. With proper calibration, a visual match of emission intensity can allow oxygen estimations to within a few percentiles.

For sensor 10, films of 0.001" thickness, the response time is subsecond. Thicker sensor films respond more slowly and provide indications of average oxygen concentrations.

In an alternative embodiment, the present invention contemplates the use of a self-referencing sensor. Such a sensor includes a mixture of fluorophors which have differing sensitivities to oxygen quenching and differing colors of emission. By suitably adjusting the characteristics, the sensor is made to change colors at different oxygen concentrations. It is thus possible to completely dispense with the reference emitter 12 used with the system described above. The self-referencing sensor is especially useful in go - no go applications.

The mixing of two different colored luminescent chromophores as an oxygen paper is an entirely new concept. For example, if a quenchable green emitter is mixed in the right proportions with an unquenchable red emitter, an apparently green emission results in the absence of quencher. But as the green component is quenched by raising the quencher concentration, the color will shift smoothly from green to orange to red. Each color during this transition will correspond to a characteristic oxygen concentration. The range and color transition can be varied by varying the concentration and the nature of the sensor.

The referencing systems described above are inexpensive and provide stable, long lasting, rapid monitors for gaseous or liquid oxygen levels. They can be incorporated into operating room gas lines, breathing masks, and other hospital devices where the shut-off or improper connection of oxygen could be fatal. They can also be used in mines and industrial areas where oxygen levels vary. Applications as far reaching as space capsules and as ordinary as welding machines (He-arc purges) are also contemplated. Other sensor materials may be incorporated into the polymer which sense gases other than oxygen, for example sulphur dioxide, carbon dioxide and chlorine.

A specific working embodiment will now be described as to its best mode, the method of manufacture and the method for using the invention. This is for the most part a detailed study on the use of a luminescence quenched oxygen sensor based on a luminescent metal complex, tris-(4,7-diphenyl-1,10-phenanthroline)ruthenium(II) perchlorate, i.e., $[Ru(Ph_2phen)_3](ClO_4)_2$, immobilized in a solvent impermeable—gas permeable polymer film. The degree of quenching of the excited complex is related to the partial pressure of $O_2$ in contact with the film. A variety of potential interferents has been examined and the limitations of the sensor are discussed.

The core of the invention is the indicator $[Ru(Ph_2phen)_3](ClO_4)_2$ immobilized and embedded in a transparent silicone rubber. A number of polymer films were examined. These included the silicone rubbers GE361, GE RTV108, GE RTV615, which are hardware store varieties of Dow Corning silicone rubber. Plexiglass, polyvinylchloride, polystyrene and polycarbonate were also tried. All data reported here is for the silicone rubber RTV-118, which is a one part polymer similar to clear bathtub sealer.

The cured polymer does not stick to plexiglass and this characteristic was exploited to form thin films with good optical quality. The uncured polymer was clamped between two plexiglass plates. Teflon, shim stock, or aluminum foil spacers were used to form uniform films of different thicknesses. The Teflon was used to form 0.001" thick films. The shim stock was used to form 0.004" thick films. The aluminum foil spacers were used to form 0.001" thick films. The films were cured in water and took several days since exposure was limited to the edges. The cured films were washed twice in dichloromethane prior to use in subsequent experiments.

Impregnation of the films with the sensor involved exploiting the fact that dichloromethane does not dissolve the cured films but does penetrate and greatly expands them to almost twice their thickness. In a typical experiment, the dry films were immersed in $1 \times 10^{-3}$ molar of the indicator $[Ru(Ph_2phen)_3](ClO_4)_2$ in dichloromethane. The concentration in the film could be controlled by adjusting the concentration of the complex in dichloromethane. The films rapidly swelled and took up the metal complex. In ten minutes the films were removed, rinsed rapidly in dichloromethane solvent to remove any surface contamination, and air dried.

It should be noted that the indicator $[Ru(Ph_2phen)_3](ClO_4)_2$ was prepared and purified according to the method of Watts, R. J.; Crosby, G. A., J. Am. Chem. Soc. 1971, 93, 3184.

All of the experiments reported here used films that were simply removed from the dichloromethane solution, rinsed rapidly in fresh dichloromethane and permitted to dry in the air. The very rapid solid evaporation and air caused the films to curl and also caused water condensation on the surface. This degraded the optical quality of the films. Films prepared this way had obvious visual non-uniformities in their concentration of sensor. It has been found that this non-uniformity can be avoided by slow evaporation of the dichloromethane in a jar with a loose fitting cardboard lid and containing a small amount of dichloromethane. Film uniformity has been improved to the point that no visual variations in the sensor concentration are detectable. Regardless of the method of sample preparation, all doped or undoped GE RTV-118 films were slightly cloudy.

The formed silicone sensor films were found to stick tenaciously to glass surfaces. In the quenching measurements, doped polymer films were placed on the insides of small square bottles, and the bottles were connected to a vacuum top and manometer. The luminescence lifetimes and luminescence intensity versus partial pressure were measured in two separate experiments. In addition to Stern-Volmer data, experiments were performed to determine hysteresis and reproducibility.

Investigations were undertaken to determine the variation of the sensor response depending on whether the sensor was in a gas stream or an aqueous solution. This was done by comparing the lifetime of sensor films in an evacuated, air or oxygen filled bottle with that of the same sensor film in a water filled bottle that was bubbled with a vigorous stream of nitrogen, air, or oxygen.

Excited state lifetime measurements were made on a microcomputerized apparatus described by Turley T. J.; M. S. Thesis, University of Virginia, 1979. Samples were excited at 337 nanometers with a Molectron nitrogen laser. Luminescence intensity measurements were made with a microcomputerized SLM model 8000 spectrofluorimeter using 450 nm excitation. Lifetime and intensity measurements were made from the front surface of the device in FIG. 5 because the sample thickness precluded the customary 90 degrees of viewing. The emission intensity was monitored at the uncorrected emission maximum of 610 nanometers. Absorbence measurements were made using a Varian model 634 spectrophotometer. Homemade manometers and valves were used in measurements involving partial pressures. All measurements were made at room temperature, i.e., 23°±3° C.

Interference studies were carried out in two ways. A variety of solutions are potentially capable of quenching the luminescence, destroying the complex, or extracting it from the film. To monitor leaching or destruction of the complex, the spectrophotometric method was used. The absorbence at the absorption maximum was measured before and after a 24 hour exposure to the selected solution. Interferents included a surfactant, a strong oxidant, a reducing agent, a strong acid, a strong base, a strong complexing agent, and organic solvents.

In the second set of studies, the films were exposed to one excellent aqueous solution quencher and several gases of physiological or chemical importance. Interference was monitored by changes in luminescence lifetime or intensity on introduction of the interferent to the evacuated or $N_2$ purged sample cell. The ionic quencher was $Fe^{3+}$. The gases were the anesthetics $N_2O$, cyclopropane and Halothane. Other gases were refrigerant Genetron 118, the sterilent chlorine, or $Cl_2$ from commercial bleach solutions, and the industrial pollutants sulfur dioxide and hydrogen sulfide were checked as well. Because of the possible interference of back diffusion of pump oil and because of the interest in petroleum products, the sensor was also immersed in vacuum pump oil. In each case where quenching occurred the sensor was tested for recovery by re-evacuating or re-purging the cell.

Investigations were undertaken to determine the response time by the lifetime method of a 0.004" film stuck to a glass wall. The cell was initially evacuated and the lifetime was measured. The sample was then abruptly opened to the air and the lifetime was measured after fixed delay times. The experiment was repeated to obtain a lifetime versus time profile. The uncertainty in the time display was less than one second.

The invention was tested to determine rapidly changing oxygen concentrations which might occur in a patient's breath. These investigations were undertaken using the primitive breath monitoring cell of FIG. 5 but where the film was suspended in the middle of the cell so as to expose both sides. To enhance response time a 0.001" thick film was mounted so that both sides of the film were exposed to the gas flow. The spectrofluorimeter was set to its fastest integration time, i.e., 0.02 second. Two gas flow configurations were used. A two-way stop lock, or T, was set up so that rapid flows of either nitrogen or air could be switched to flow over the sensor film. Intensity measurements were started and the gas flow was switched. This process was repeated several times.

In the breathing experiments, the T was disconnected and a person breathed through a ⅜ inch wide, two foot long rubber tube while the spectrofluorimeter recorded luminescence intensities as a function of time. In a second experiment the breath was held for about 17 seconds and then normal breathing resumed.

Figure 5:
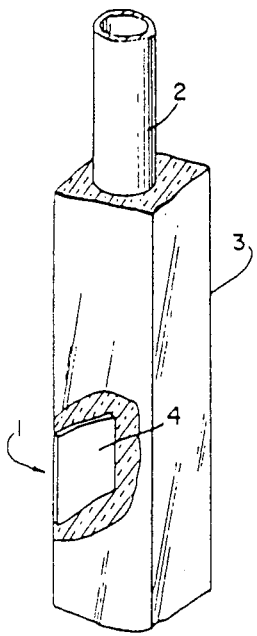
FIG. 5 is a diagrammatic presentation of a breathing cell.

To test temperature effects the cell of FIG. 5 was filled with cooled or heated deoxygenated water and lifetime measurements were quickly made. Because of a lack of suitable equipment, only temperature effects on the excited state lifetime, rather than on the quenching constant, were made.

The indicator $[Ru(Ph_2phen)_3](ClO_4)_2$ was selected as a sensor material for several reasons. Luminescent Ru(II) complexes exhibiting charged transfer luminescences exhibit high photochemical stability and rather long-lived excited states. The long-lived excited states are measured in microseconds. These ruthenium(II) complexes also exhibit a unique emission. The indicator $[Ru(Ph_2phen)_3]^{2+}$ has an absorption spectrum that peaks at 460 nanometers and extends to beyond 500 nanometers, which gives flexibility in the excitation region. Its molar absorptivity at the visible maximum is 30,000 and is relatively broad, which permits low concentrations to be used and further decreases the stringency of the excitation wavelength requirements. Its emission is well separated from the absorption, i.e., greater than 600 nanometers, which eliminates reabsorption problems and minimizes spectral filtering difficulties.

Moreover, in aqueous solutions the unquenched photon yield of $[Ru(Ph_2phen)_3]^{2+}$ approaches 0.5, Nakamaru, K.; Nishio, K.; Nobe, K.; Sci. Rep. Hirosaki Univ. 1979, 26 57. Given the similar solution and polymer-immobilized lifetimes, the luminescence yield in the RTV-118 is probably very nearly the same. The high luminescence efficiency in the sensor reduces sensor sensitivity to scattering interferences and permits use of less sensitive detectors. Finally, of all the Ru(II) complexes we have examined, $[Ru(Ph_2phen)_3]^{2+}$ also has the longest excited state lifetime ($>5$ $\mu s$) and the largest solution Stern-Volmer quenching constant, Demas, J. N.; Harris, E. W.; McBride, R. P.; J. Am. Chem. Soc. 1977 99, 3547.

The high photochemical stability of the Ru(II) complex is in contrast to most phosphorescent organic luminophores. The single emission of Ru(II) complexes is also in marked contrast to phosphorescent organic molecules, which invariably exhibit some degree of fluorescence and phosphorescence, each with a greatly different oxygen quenching sensitivity. Thus, with many organic luminophores the total emission and decay curves are superpositions of two components of different lifetimes. This greatly complicates data acquisition and reduces the accuracy of concentration measurements based on intensity or lifetime quenching.

RTV-118 was selected as the polymer support after examining a variety of other systems. Several had better optical properties or were easier to form (two-part polymers), but the oxygen Stern-Volmer constant was greater for our complex in the RTV-118 than any other polymer tested. Furthermore, some were difficult or impossible to dope or fabricate (e.g. PVC, polystyrene, polycarbonate) into desired shapes, were soluble in common solvents (e.g. polystyrene, Plexiglas), or had lower stability.

The unquenched excited state lifetimes at different temperatures were 5.8 $\mu$sec at 0° C., 5.9 $\mu$sec at 25° C., 4.8 $\mu$sec at 38° C., and 3.3 $\mu$sec at 60° C. These results are consistent with the well known temperature effects on the solution luminescence properties of Ru(II) complexes, Van Houten, J.; Watts, R. J.; J. Am. Chem. Soc. 1976, 95, 5159. With a simple temperature correction scheme, the quenched sensor should be quite useful up to the physiological temperature of 37° C. Higher temperatures would result in the severe drop in lifetime and yield.

The lifetime in deaerated, aerated, and oxygenated water were the same, i.e., less than 2-3 percent, as that obtained for a vacuum, air, and oxygen, respectively. This is what is expected if water vapor were not a quencher and the sensor only responds to the partial pressure of the oxygen.

Figure 6:
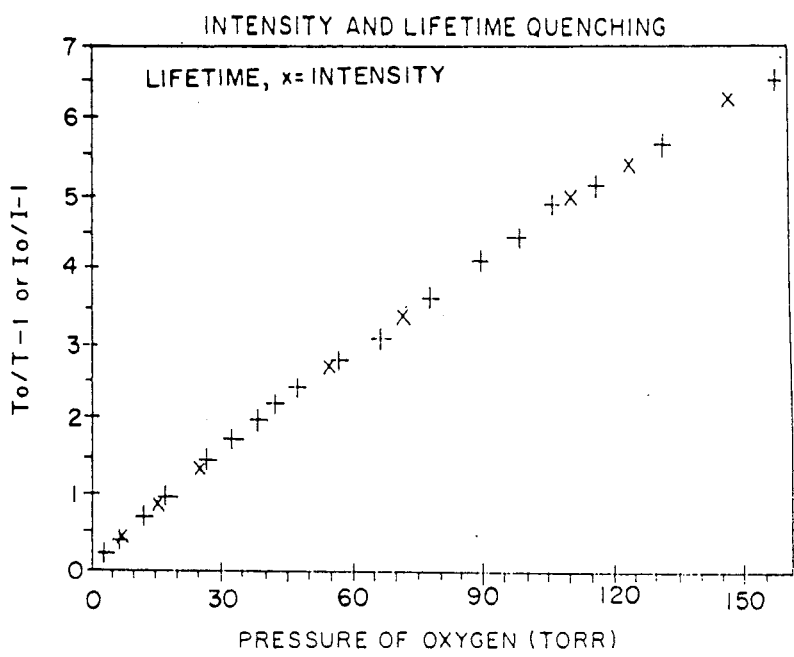
FIG. 6 is a graph comparison of lifetime (t) and intensity (x) quenching plots for 0.004" sensor film.
Figure 7:
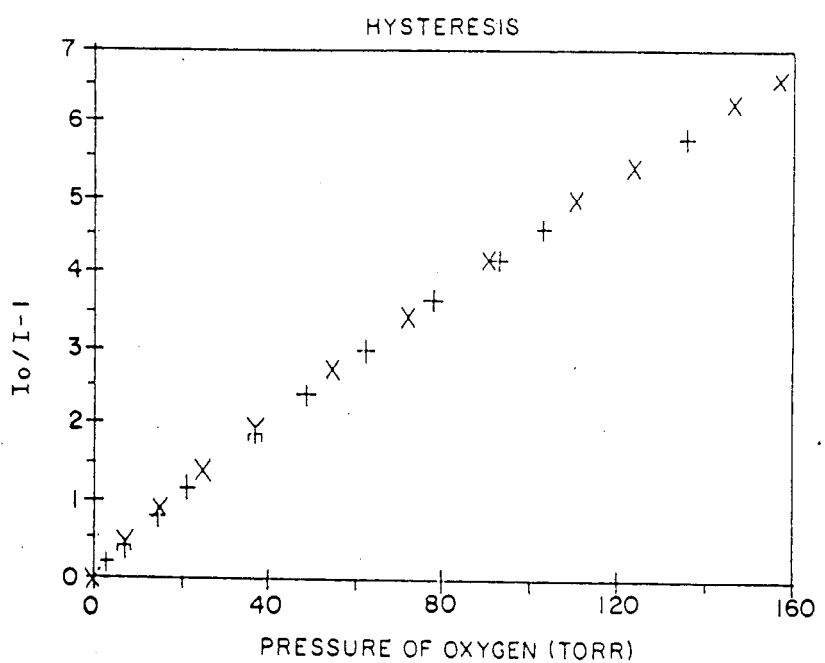
FIG. 7 is a graph of a hysteresis plot for luminescence of sensor film exposed to decreasing (x) and then increasing (t) oxygen partial pressures.

FIGS. 6 and 7 show intensity and lifetime Stern-Volmer quenching plot for the RTV system. Unlike solution Stern-Volmer measurements, the Stern-Volmer calibration curves for the polymer films always exhibited some downward curvature. The film calibration plots were, however, highly reproducible, which is the primary consideration for an analytical technique.

In spite of the non-linear Stern-Volmer plots, intensity and lifetime measurements gave calibration curves that were indistinquishable (FIG. 6). The sensors exhibited no hysteresis as shown in FIG. 7, where the data were taken as the partial pressure of $O_2$ decreased (x) and then increased (+).

Sensor reproducibility was apparently limited by instrument drift and inhomogeneity of the complex in the sensor films. For ten air-to-$N_2$-to-air cycles the relative standard deviation, i.e., RSD, for the emission intensity in air was 3.4 percent and that in $N_2$ was 3.7 percent, but the RSD for paired nitrogen-to-air intensity ratios was 0.54 percent. Thus, instrumental drift was indicated.

With lifetime measurements the $N_2$ values yielded an RSD of 0.38 percent, where n=5, when the sample was not moved, and 2.51 percent, where n=5, when the same film was repositioned between readings. This film also showed an RSD of 2.0 percent, where n=5, when it was in air and was not repositioned. The higher noise for the air sample is attributed to the fact that the relative noise increases with the decreasing luminescent intensity of the quenched sample. Because of the inhomogeneity of the films used in this study, it is expected that the enhanced preparation procedure described in the experimental section would produce a more uniform sensor.

The non-linearities of the Stern-Volmer plots is attributed to inhomogeneities in the binding sites in the polymer and, thus, differences in the local oxygen quenching constants. This conclusion is supported by several facts. The downward curvature is characteristic of multiple species. The decay curves appear to have some degree of non-exponentiality in the more heavily oxygen quenched samples. Sulfur dioxide quenched samples exhibit gross non-exponentialities. The observed non-exponentialities are consistent with $SO_2$ being less mobile and bulkier than oxygen, which amplifies lifetime differences for different binding regions.

The solution stability tests are summarized in Table 1. The surfactant and the reducing agent are without detectable effect on the complex concentration.

TABLE 1

Absorbance Before and After Exposure to Chemicals for 24 hours

| Chemical | Type | Absorbance Before | Absorbance After | % Change |
|---|---|---|---|---|
| 0.05M NaLS | Surfactant | 1.46 | 1.46 | 0 |
| 0.1M EDTA—0.5M NaOH | Complexing | 1.10 | 1.15 | +4.5 |
| 0.1M $Na_2S_2O_4$ | Reducing | 1.27 | 1.27 | 0 |
| 0.1M $K_2Cr_2O_7$—0.1M $H_2SO_4$ | Oxidizing | 1.22 | 1.21 | −0.8 |
| 1.0M NaOH | Base | 1.36 | 1.67 | +22.8 |
| 1.0M HCl | Acid | 1.30 | 1.12 | −13.8 |
| Acetone | Organic | 1.23 | 0.42 | −67.2 |
| 95% Ethanol | Organic | 1.45 | 1.47 | +1.4 |

Both the EDTA and the NaOH solution are basic and cloud the polymer surface. This increases light scattering, which appears as increased absorbence. Within our experimental error, however, there was no discernible destruction of the complex.

The HCl results suggest that the acid might leach the complex, however, the $K_2Cr_2O_7$ solution was nearly as acidic, but showed no leaching. We, therefore, attribute the apparent loss of complex to non-uniformity in the concentration of the complex across the film or in film thickness, and the difficulty of reproducibly positioning the film in the spectrophotometer.

There was no quantitative evidence for leaching of the complex into ethanol, even though ethanol is an excellent solvent for the complex. Similarly, methanol does not extract any $[Ru(Ph_2phen)_3]^{2+}$ from the film as judged by the absence of color or luminescence in methanol in which the films were soaked. Acetone, however, swelled the polymer and leached the complex out of the film as indicated by coloration and luminescence of the solvent.

Table 2 summarizes the quenching studies. The excellent solution quencher $Fe^{3+}$ is without effect. The physiologically and medically important gases $CO_2$, nitrous oxide, cyclopropane, and Halothane are all without effect at concentrations well above those normally encountered. The halocarbon refrigerant Genetron is without effect as is pump oil and the common petroleum industry pollutant $H_2S$.

TABLE 2

Effect of Interferents on Excited State Lifetime or Intensity

| Chemical | Type[a] | Lifetime (μs) or Intensity | | |
|---|---|---|---|---|
| | | Before | During | After |
| Fe(NO$_3$)$_3$[b] | Qu | 6.48 | 6.31 | — |
| Bleach (Cl$_2$) | Ox, Q | 5.95 | 5.45 | 5.83 |
| SO$_2$ | Q | 4.69 | 0.94 | 5.72 |
| Cyclopropane | An | 5.77 | 5.32 | 5.84 |
| Gentron | An | 5.79 | 5.92 | 5.81 |
| CO$_2$ | G | 5.51 | 5.33 | 5.50 |
| H$_2$S | G | 1.000[c] | 1.000[c] | |
| N$_2$O | G, An | 5.55 | 5.46 | 5.46 |
| Pump Oil | O | 5.42 | 5.19 | — |
| Halothane | R | 5.49 | 5.36 | — |

[a]Ox = oxidant, Q = quencher, O = organic, An = anesthetic, R = refrigerant, G = gas.
[b]0.01M in 0.1M HNO$_3$.
[c]Relative emission intensity. Estimated accuracy ± 1%.

The Halothane and nitrous oxide results are significant as Halothane is the operating room anesthetic of choice in the United States, and nitrous oxide is the primary gaseous dental anesthetic. Halothane, because of its ease of reduction, is a severe interferent for the Clark electrode. Indeed, at physiological concentrations, Halothane produces signals that correspond to oxygen partial pressures in excess of an atmosphere, even in the complete absence of oxygen. Alberty, W. J.; Hahn, C. E. W.; Brooks, W. N.; Br. J. Anaesth. 1981, 53, 447.

It was feared that because the excited state of Ru(II) complexes are powerful oxidants and reductants, Hauenstein, Jr., B. L.; Mandal, K.; Demas, J. N.; DeGraff, B. A.; Inorg. Chem. 1984, 23, 1101, easily reduced gaseous species such as H$_2$S would be interferents. Results, however, show that there is no detectable quenching by H$_2$S even at a full atmosphere.

Only chlorine and SO$_2$ were effective quenchers. We consider the small degrees of apparent quenching in the remaining cases as arising from small air leaks in our vacuum system or the inability to exclude traces of air when we introduced the potential quencher. Chlorine introduced from common household bleach quenched the lifetime. The recovery of the emission and lifetime, however, was complete after the bleach was removed by rinsing with water. We suspect that excited state oxidative quenching of the complex is occurring.

Figure 8:
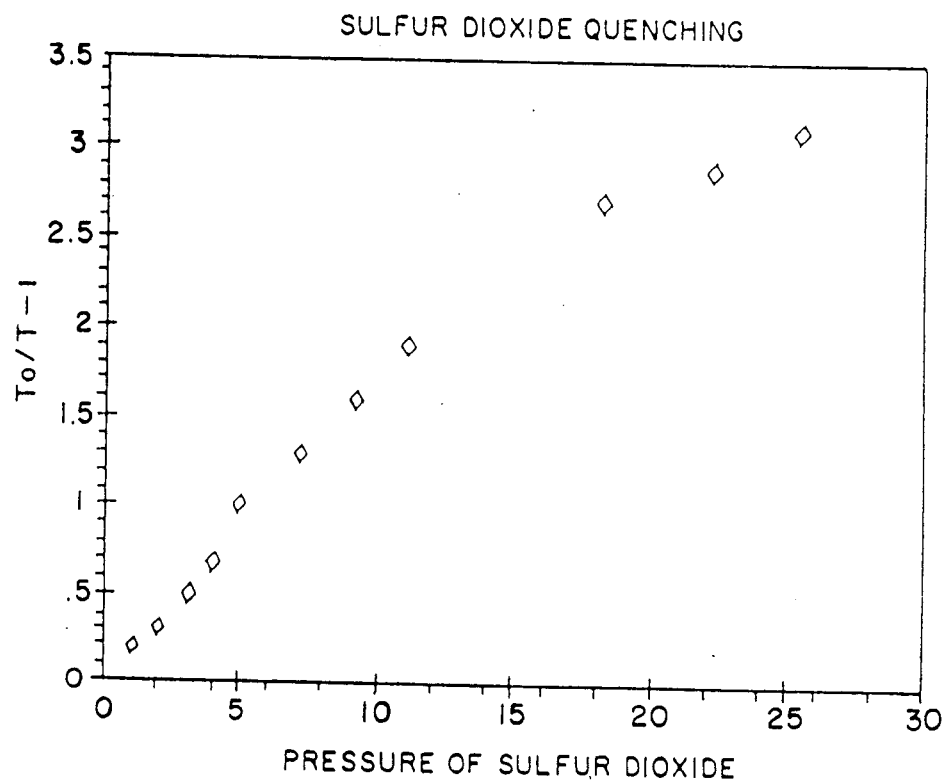
FIG. 8 is a graph of lifetime Stern-Volmer quenching by $SO_2$.

Sulfur dioxide is an especially severe interferent. A lifetime Stern-Volmer plot is shown in FIG. 8. Not only is quenching severe at low SO$_2$ partial pressures, but the decay curves are extremely non-exponential. Thus, it would be virtually impossible to use the sensor in the presence of appreciable SO$_2$ concentrations. We attribute the quenching to an excited state electron transfer reaction with the SC$_2$.

In summary, quenchers, solutions, or solvents that do not penetrate into the polymer will not affect the sensor concentration, degrade the sensor, or distort the response. Good solvents for the complex, which penetrate and swell the film, such as acetone and CH$_2$Cl$_2$ destroy the sensor. Somewhat surprising is that relatively polar organic solvents such as ethanol are also barred from penetrating into the polymer and, thus, do not degrade the sensor. While virtually all small gaseous molecules will penetrate the sensor film, we have found few which are detrimental.

Figure 9:
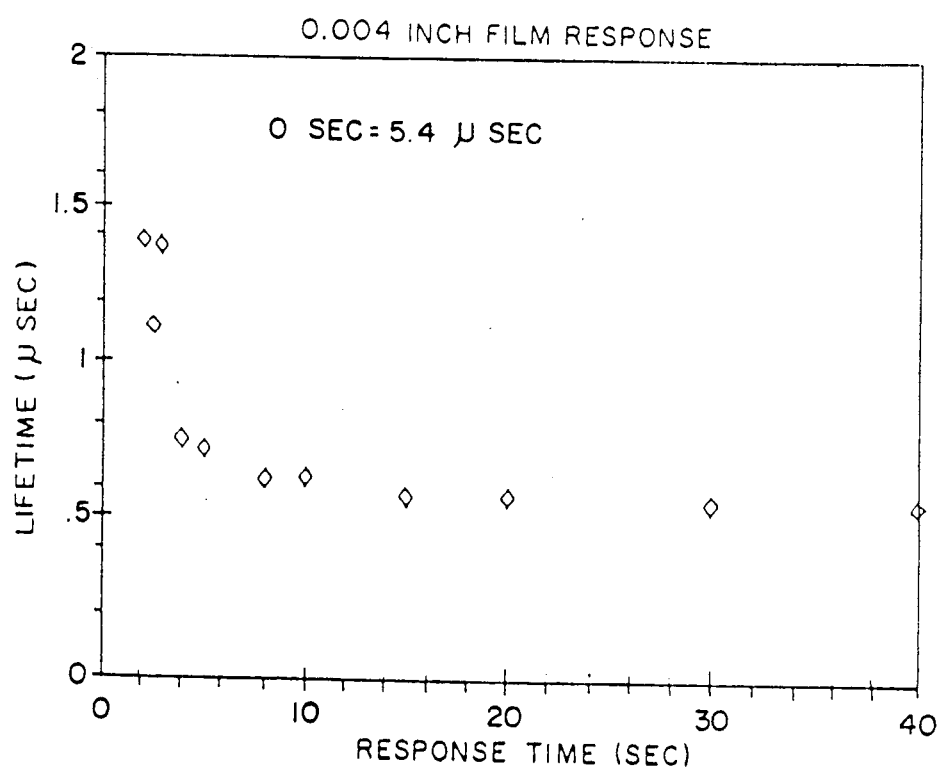
FIG. 9 is a graph of a time response of a 0.004" film stuck to a glass wall on release of the vacuum to air. The initial evacuated lifetime was 5.4 microseconds, i.e. 5.4 S.

FIG. 9 shows the response time of the 0.004" film when air is suddenly introduced into the evacuated cell. The response time to 95 percent of the final value is 3 s.

Figure 10:
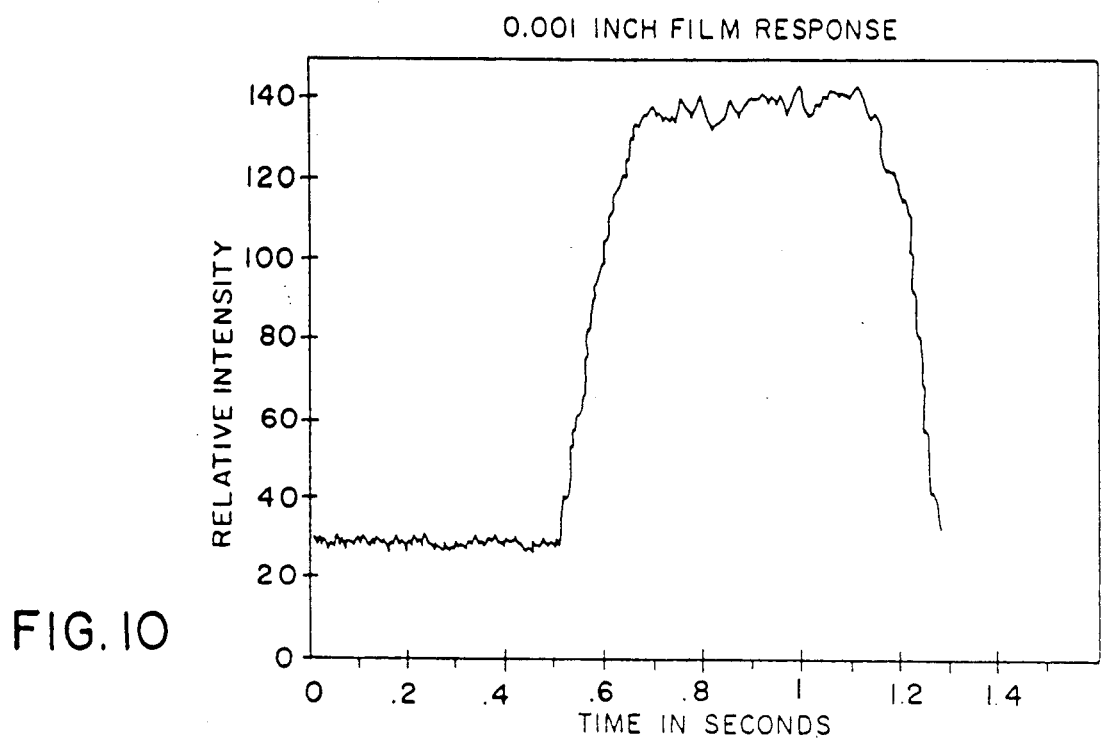
FIG. 10 is a graph of the response of a 0.001" sensor in the cell of FIG. 5 when subjected to step changes in the oxygen concentration.
Figure 11:
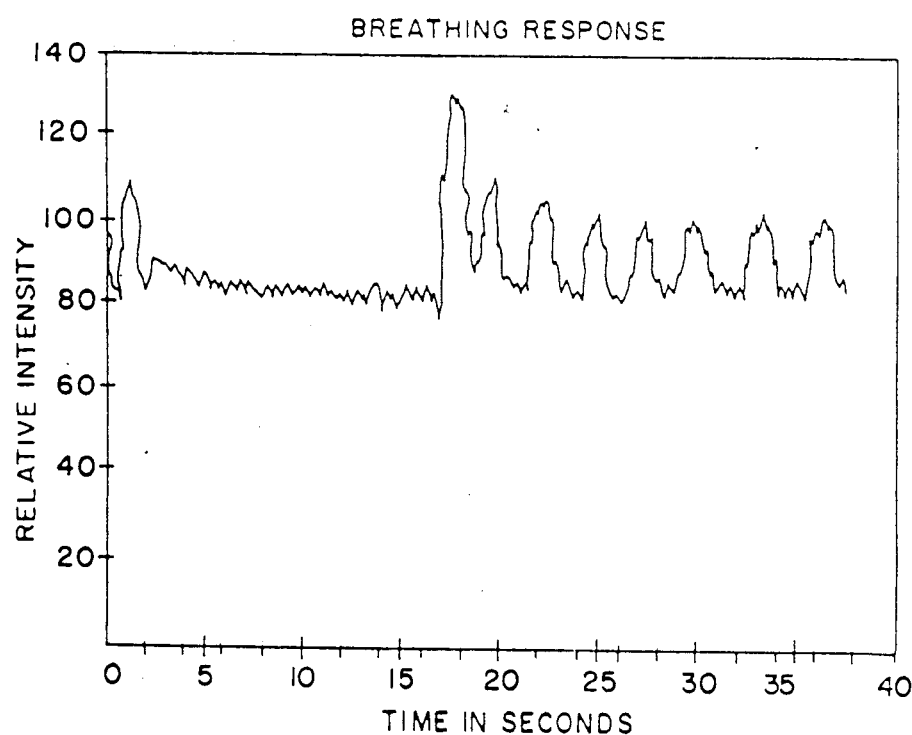
FIG. 11 is a graph of the response of the sensor cell of FIG. 5 when subjected to breathing. Normal breathing would correspond to the rightmost three breaths.

FIG. 10 shows the response of the 0.001" thick film to step changes in the oxygen concentration. The terminal intensity is reached in <0.18 s irrespective of whether the change is from air to nitrogen or nitrogen to air. The actual response may be faster than this since the purging time in the gas lines could not be controlled. The breathing studies in FIG. 11 indicate that the thin film sensor responds fast enough to faithfully follow oxygen concentrations while breathing. Of particular interest is the luminescence intensity following breath holding. The higher emission intensity on the first exhalation arises from the decreased oxygen concentration due to the increased exchange time in the lungs. The several breaths for the lungs to re-equilibrate are also clearly visible. No attempt was made to obtain quantitative oxygen measurements in the breathing experiments because the breathing was into a sealed spectrophotometer compartment and the gas flow over the sensor did not guarantee complete exchange.

To summarize, an optical method for determining oxygen in both gaseous and fluid samples has been developed. The method employs lifetime or emission intensity reduction in the presence of quencher. The system is a unified sensor-membrane system that includes a highly luminescent [Ru(Ph$_2$phen)$_3$]$^{2+}$ immobilized in a silicone rubber matrix. The hydrophobic matrix excludes a variety of potential solution interferents (e.g. surfactants, complexing agents, oxidants, reductants, acids, and bases) while permitting free access of oxygen to the sensor. A variety of medical, physiological, and industrial gases do not interfere. SO$_2$ and Cl$_2$ do interfere, but they do not degrade the sensor for future use. While strong base does fog the exposed surface of the sensor, this would not affect the response to lifetime measurements or of intensity methods which do not utilize the solvent exposed face. Solvents that swell the matrix can, however, destroy the sensor.

The excited state lifetime of the complex is long enough to permit measurements with relatively unsophisticated and inexpensive equipment, Demas, J. N.; J. Chem. Ed. 1976, 80, 2248. This is in contrast to the expensive instrumentation required to measure the short fluorescence lifetimes of organic compounds.

The method does not consume oxygen and the sensor films are stable for years. The sensor can be fabricated in a variety of configuration depending on the application and the response time required. Thicker films, for example, can be used to average the concentration over several seconds or minutes to prevent the response to short term excursions: this could replace a long time constant averaging circuit. Excited state lifetime measurements can be used in place of intensity quenching measurements when the necessary geometric or source stability is inadequate for long term intensity measurements.

The current system can be used to analyze oxygen concentrations to below 1 Torr partial pressure of oxygen. Lower sensitivity sensors could be fabricated using less permeable polymers or sensor complexes with shorter excited state lifetimes.

As this invention may be embodied in several forms without departing from the spirit or essential characteristics thereof, the present embodiments are therefore illustrative and not restrictive, and since the scope of the invention is defined by the appended claims all changes that fall within the metes and bounds of the claims or that form their functional as well as conjointly cooperative equivalents are therefore intended to be embraced by those claims.

We claim:

1. An apparatus for measuring oxygen concentration comprising
   - a sensor made of luminescent material;
   - a polymer barrier covering the sensor, wherein the polymer is permeable to oxygen;
   - means for exciting the sensor with a modulated light source to generate luminescence therein; and
   - means for measuring a phase shift of luminescence generated in the sensor to determine luminescence lifetime, wherein any quenching related to decreases in lifetime due to the presence of oxygen are indicative of concentration of oxygen, wherein the barrier comprises light transmissive cured silicone rubber having tris-(4,7-diphenyl-1,10-phenanthroline)ruthenium(II) perchlorate immobilized therein as the luminescent material.